(12) United States Patent  (10) Patent No.: US 7,214,702 B2
Sharma  (45) Date of Patent: May 8, 2007

(54) PROCESS FOR PRODUCING A DIPEPTIDYL PEPTIDASE IV INHIBITOR

(75) Inventor: Padam N. Sharma, Manlius, NY (US)

(73) Assignee: Bristol-Myers Squibb Company, Princeton, NJ (US)

(*) Notice: Subject to any disclaimer, the term of this patent is extended or adjusted under 35 U.S.C. 154(b) by 185 days.

(21) Appl. No.: 11/135,217

(22) Filed: May 23, 2005

(65) Prior Publication Data

US 2005/0267191 A1 Dec. 1, 2005

Related U.S. Application Data

(60) Provisional application No. 60/574,177, filed on May 25, 2004.

(51) Int. Cl.
*A61K 31/403* (2006.01)
*C07D 209/04* (2006.01)

(52) U.S. Cl. ..................... 514/412; 548/452

(58) Field of Classification Search ............. 514/412; 548/452
See application file for complete search history.

(56) References Cited

U.S. PATENT DOCUMENTS

| 6,068,991 | A | 5/2000 | Liu et al. |
| 6,395,767 | B2 | 5/2002 | Robl et al. |
| 2005/0090539 | A1 | 4/2005 | Vu et al. |

FOREIGN PATENT DOCUMENTS

| EP | 0 808 824 | 11/1997 |
| WO | WO 00/04179 | 1/2000 |

OTHER PUBLICATIONS

U.S. Appl. No. 11/091,183, filed Mar. 28, 2005, Sharma et al.
U.S. Appl. No. 11/104,015, filed Apr. 12, 2005, Politino et al.
U.S. Appl. No. 11/119,552, filed May 2, 2005, Patel et al.
Hanessian, S. et al., "Probing the Importance of Spacial and Conformational Domains in Captopril Analogs for Angiotensin Converting Enzyme Activity", Bioorganic & Medicinal Chemistry Letters, vol. 8, pp. 2123-2128 (1998).
Hanson, R.L. et al., Synthesis of allysine ethylene acetal using phenylalanine dehydrogenase from *Thermoactinomyces intermedius*, Enzyme and Microbial Technology, vol. 26, pp. 348-358 (2000).
Imashiro, R. et al., "Asymmetric synthesis of methyl (2R,3S)-3-(4-methoxyphenyl) glycidate, a key intermediate of diltiazem, via Mukaiyama aldol reaction", Tetrahedron Letters, vol. 42, pp. 1313-1315 (2001).
Reetz, M.T. et al., "General Synthesis of Potentially Antiviral α-Adamantyl Carbonyl Compounds", Angew. Chem. Int. Ed. Engl., vol. 18, No. 1, p. 72 (1979).

Reetz, M.T. et al., "Lewis-Säure-bedingte α-*tert*-Alkylierung von Carbonsäuren und Carbonsäureestern", Chem. Ber., vol. 116, pp. 3708-3724 (1983).
Reetz, M.T. et al., "Regioselektive Lewis-Säure-bedingte α-*tert*-Alkylierung von Acyloinen und Glycolsäure", Chem. Ber., vol. 116, pp. 3702-3707 (1983).
Sagnard, I. et al., "Enantioselective Synthesis of Cyclopropane α-Amino Acids: Synthesis of N-Boc-*cis*-(2S,3R,4S)-3,4-Methanoproline and N-Boc-(2S,3R,4S)-3,4-Methanoglutamic Acid", Tetrahedron Letters, vol. 36, No. 18, pp. 3148-3152 (1995).
Takada, H. et al., "Thermostable Phenylalanine Dehydrogenase of *Thermoactinomyces intermedius*: Cloning, Expression, and Sequencing of Its Gene", J. Biochem., vol. 109, pp. 371-376 (1991).
Tverezovsky, V.V. et al., "Synthesis of (2S, 3R, 4S)-3,4-Methanoproline and Analogues by Cyclopropylidene Insertion", Tetrahedron, vol. 53, No. 43, pp. 14773-14792 (1997).

*Primary Examiner*—Kamal A. Saeed
(74) *Attorney, Agent, or Firm*—Burton Rodney

(57) ABSTRACT

A process is provided for preparing the dipeptidyl peptidase of the structure I

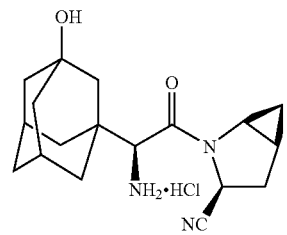

(also referred to as saxaglipitin)
by direct dehydration, in one pot, of the amide II

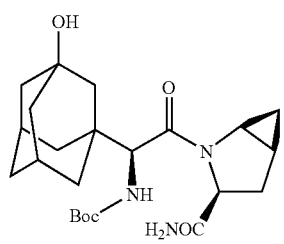

by reacting amide II with phosphorus oxychloride in an organic solvent such as dichloromethane, quenching the reaction mixture with water to form the hydrochloric acid salt of I, and treating the hydrochloric acid salt with base to form the free base of I.

16 Claims, No Drawings

PROCESS FOR PRODUCING A DIPEPTIDYL PEPTIDASE IV INHIBITOR

This application claims a benefit of priority from U.S. Provisional Application No. 60/574,177, filed May 25, 2004, the entire disclosure of which is herein incorporated by reference.

FIELD OF THE INVENTION

The present invention relates to a process for preparing (1S,3S,5S)-2-[(2S)-2-amino-2-(3-hydroxytricyclo[3.3.1.1$^{3,7}$]dec-1-yl)-1-oxoethyl]-2-azabicyclo[3.1.0]hexane-3-carbonitrile which is an inhibitor of dipeptidyl peptidase (DPP) IV and thus is useful in the treatment of diabetes and complications thereof, hyperglycemia, Syndrome X, hyperinsulinemia, obesity, and atherosclerosis and related diseases, as well as immunomodulatory diseases and chronic inflammatory bowel disease.

BACKGROUND OF THE INVENTION

Dipeptidyl peptidase IV is a membrane bound non-classical serine aminopeptidase which is located in a variety of tissues including, but not limited to, intestine, liver, lung, and kidney. This enzyme is also located on circulating T-lymphocytes wherein it is referred to as CD-26. Dipeptidyl peptidase IV is responsible for the metabolic cleavage of the endogenous peptides GLP-1(7-36) and glucagons in vivo and has demonstrated proteolytic activity against other peptides such as GHRH, NPY, GLP-2 and VIP in vitro.

GLP-1(7-36) is a 29 amino acid peptide derived from post-translational processing of proglucagon in the small intestine. This peptide has multiple actions in vivo. For example, GLP-1(7-36) stimulates insulin secretion and inhibits glucagon secretion. This peptide promotes satiety and slows gastric emptying. Exogenous administration of GLP-1(7-36) via continuous infusion has been shown to be efficacious in diabetic patients. However, the exogenous peptide is degraded too rapidly for continual therapeutic use.

Inhibitors of dipeptidyl peptidase IV have been developed to potentiate endogenous levels of GLP-1(7-36). U.S. Pat. No. 6,395,767 to Hamann et al. discloses cyclopropyl-fused pyrrolidine-based inhibitors of dipeptidyl peptidase IV. Methods for chemically synthesizing these inhibitors are disclosed in U.S. Pat. No. 6,395,767 as well as in the literature. For example, see Sagnard et al. Tet-Lett. 1995 36:3148–3152; Tverezovsky et al. Tetrahedron 1997 53:14773–14792; and Hanessian et al. Bioorg. Med. Chem. Lett. 1998 8:2123–2128. A preferred inhibitor disclosed in U.S. Pat. No. 6,395,767 is (1S,3S,5S)-2-[(2S)-2-amino-2-(3-hydroxytricyclo[3.3.1.1$^{3,7}$]dec-1-yl)-1-oxoethyl]-2-azabicyclo[3.1.0]hexane-3-carbonitrile, as depicted in Formulae M (HCl salt) and M' (free base),

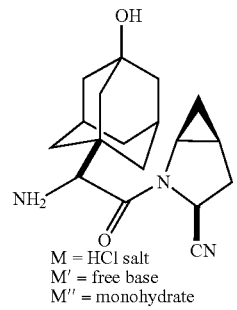

M = HCl salt
M' = free base
M" = monohydrate and the corresponding monohydrate of (1S,3S,5S)-2-[(2S)-2-amino-2-(3-hydroxytricyclo[3.3.1.1$^{3,7}$]dec-1-yl)-1-oxoethyl]-2-azabicyclo-[3.1.0]hexane-3-carbonitrile (M") (all of which are collectively referred to as saxaglipitin).

Methods adapted for preparing intermediates used in the production of this dipeptidyl peptidase IV inhibitor are disclosed in EP 0 808 824 A2. Also see, Imashiro and Kuroda Tetrahedron Letters 2001 42:1313–1315, Reetz et al. Chem. Int. Ed. Engl. 1979 18:72, Reetz and Heimbach Chem. Ber. 1983 116:3702–3707, Reetz et al. Chem. Ber. 1983 116:3708–3724.

U.S. application Ser. No. 10/716,012 filed Nov. 18, 2003 discloses a method for preparing a DPP4 inhibitor compound 4 which requires a dehydration of compound 1 using pyridine-trifluoroacetic anhydride to give a mixture of products having trifluoroacetate group protection on hydroxy and amine or both (Compounds 6 and 7) and undehydrated-O-trifluoroacetate compound 5 as minor component. The nitrites 6 and 7 of the combined mixture then undergoes a hydrolysis step to give compound 2. Compound 1 is also formed in this reaction from compound 5, leading to loss of yield. If compound 1 is present in higher amounts after hydrolysis it may be difficult to remove it during crystallization of compound 2. Compound 2 is then subjected to another chemical process to deprotect the N-Boc group to form compound 3. HCl which on basification forms compound 4.

The above is illustrated by the following reaction sequence:

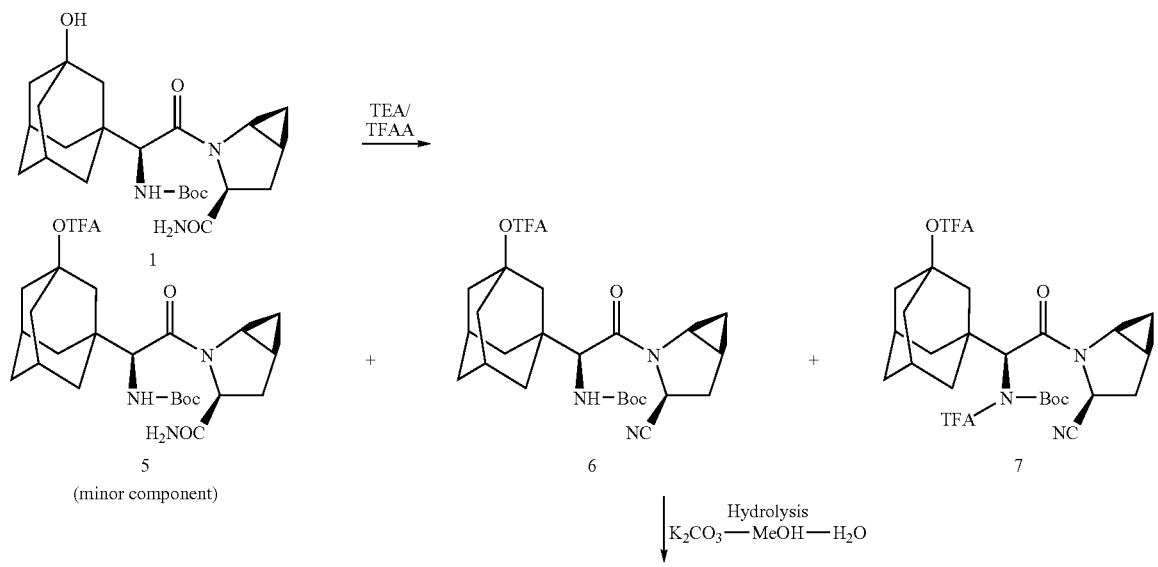

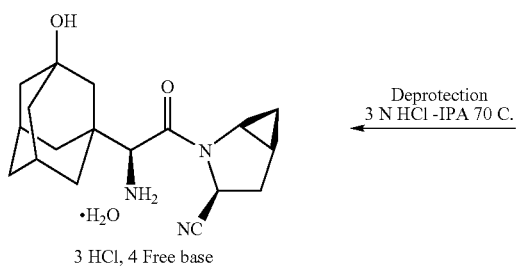

3 HCl, 4 Free base

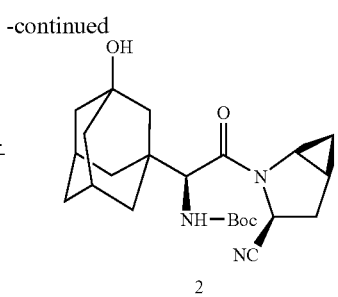

2

-continued

As can be seen from the above reaction scheme, the amide 1 is converted to the HCl salt 3 employing a three-step process wherein (1) amide 1 is made to undergo dehydration to form the cyano compounds 6 and 7; (2) the cyano compounds 6 and 7 are hydrolyzed to the alcohol 2, which is deprotected to form the HCl salt 3.

Although the above three-step procedure for producing HCl salt 3 from amide 1 is adequate, any improvement in such procedure which involves direct conversion of amide 1 to the HCl salt 3 (without the hydrolysis step) would be a most welcome improvement.

BRIEF DESCRIPTION OF THE INVENTION

In accordance with the present invention, a process is provided for preparing a compound of the structure I (also referred to as saxaglipitin)

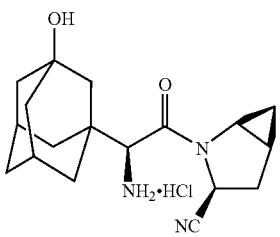

I from amide II

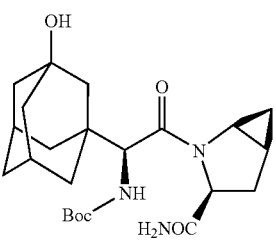

II employing a direct dehydration of the amide which contains a tertiary alcohol group and N-Boc deprotection, in preferably in one pot, thereby eliminating two chemical steps, namely hydrolysis and deprotection, ordinarily employed in previous processes as discussed above.

The process for preparing a compound of the structure I

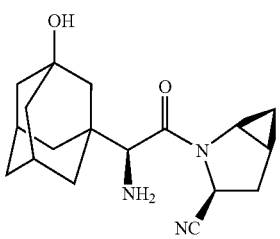

I in accordance with the present invention includes the steps of a) providing an amide of the structure II

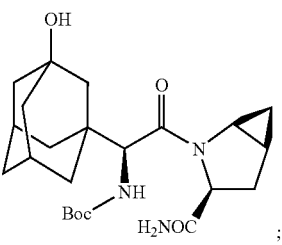

II b) reacting the amide II with phosphorus oxychloride in an organic solvent, preferably dichloromethane, to form cyano compound III

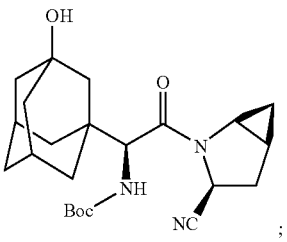

III and c) without isolating cyano compound III, admixing water with the cyano compound III to form the product of structure I in the form of the hydrochloride salt.

The process of the invention as defined above may further include the step of treating the acid salt of product I with base to form the corresponding free base.

In a preferred embodiment, the process of the invention is carried out as a one-pot process where the cyano compound III is not isolated.

In a preferred embodiment of the invention, the reaction mixture containing the amide II and phosphorus oxychloride in dichloromethane as the organic solvent is cooled to below about 5° C. and treated with water to form the hydrochloride salt. The hydrochloride salt is treated with base such as an alkali metal hydroxide such as NaOH, LiOH or KOH, to a pH within the range from about 7.0 to about 14.0 to form the product I in the form of its free base.

The phosphorus oxychloride will preferably be employed in a molar ratio to amide II within the range from about 1:1 to about 99:1.

DETAILED DESCRIPTION OF THE INVENTION

The process of the invention for forming the DPP4 inhibitor I is depicted by the following reaction scheme:

SCHEME 1

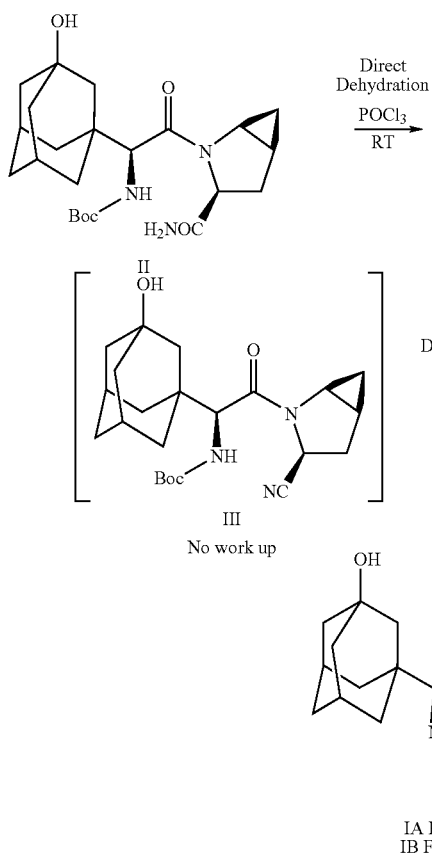

IA HCl salt
IB Free base

The above direct dehydration reaction is preferably carried out in one pot without employing a hydrolysis step.

The process is carried out by reacting amide II with a dehydrating agent, preferably phosphorus oxychloride, in an organic solvent, preferably dichloromethane.

The dehydration reaction is carried out employing a molar ratio of dehydrating agent:to amide II within the range from about 1:1 to about 99:1, preferably from about 2:1 to about 4:1. Where phosphorus oxychloride is employed as the dehydrating agent, it is preferred to employ at least 3 equivalents of phosphorus oxychloride for each equivalent of amide II.

The reaction is preferably carried out at room temperature to form cyano compound III. On quenching the reaction mixture with water, compound III is converted to the HCl salt (IA) of compound I. The resulting reaction mixture is basified for example, by addition of base such as an alkali metal hydroxide, preferably NaOH, to a pH within the range from about 7.0 to about 14.0, more preferably about 9, to form the free base IB. The free base IB is separated from the reaction mixture preferably by adding sodium chloride. The resulting organic layer containing the free base is concentrated to leave the free base IB.

Dehydration agents which may be employed herein include but are not limited to $POCl_3$, tosyl chloride, formic acid, diphosphorus tetraiodide, trimethylsilyl polyphosphate, dipyridyl sulfite, $PCl_3$, $PCl_5$, $P_2O_5$, p-nitrobenzene sulfonyl chloride, ethyl polyphosphate, sodium borohydride, or phase transfer reagents i.e. $PhCH_2NEt_3Cl$, $PhCH_2NEt_3Br$, preferably $POCl_3$.

Organic solvents which may be employed herein include but are not limited to dichloromethane, toluene, chloroform, THF, acetonitrile, methyl acetate, ethyl acetate, propyl acetate, butyl acetate, acetone, methyl isobutyl ketone, methyl ethyl ketone, 1,2-dimethoxyethane, 2-methyltetrahydrofuran, 1,4-dioxane, MTBE, chlorobenzene, xylenes, heptane, hexanes, cyclohexane, DMF, dimethyl sulfoxide, N-methylpyrrolidinone, ethanol, isopropanol, n-propanol, n-butanol or t-butanol, preferably dichloromethane.

The amide may be prepared by the following reaction scheme which is described in detail in U.S. application Ser. No. 10/716,012, filed Nov. 18, 2003, which is incorporated herein by reference.

SCHEME 2

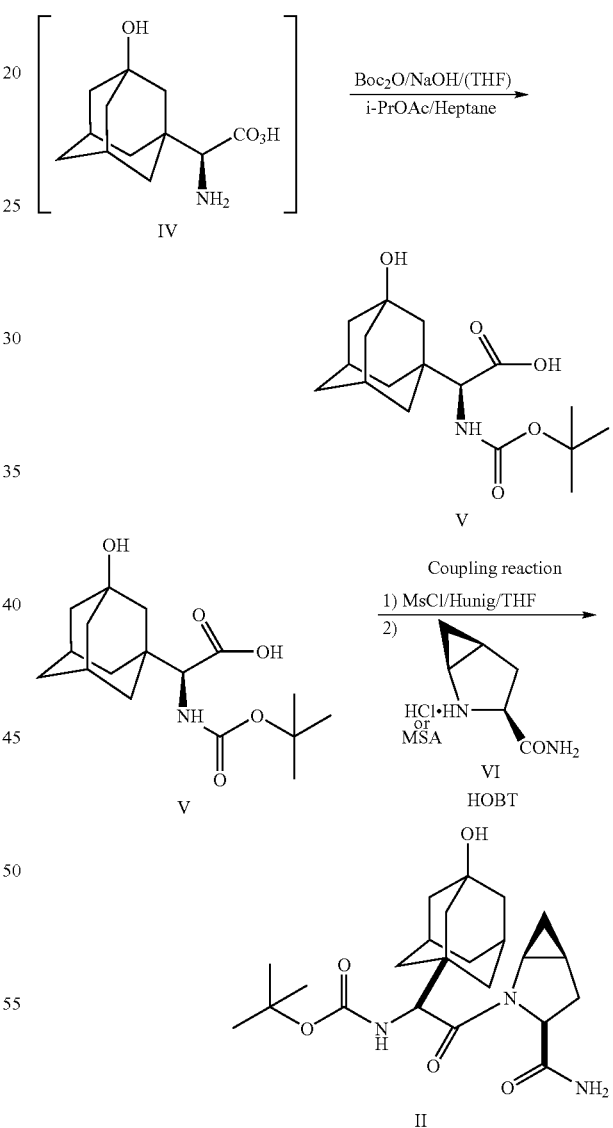

As shown in Scheme 2, the fragment (<aS)-<a-amino-3-hydroxytricyclo [3.3.1.1$^{3,7}$]decane-1-acetic acid (Formula IV) (prepared as described in U.S. application Ser. No. 10,716,012 filed Nov. 18, 2003 which is incorporated herein by reference) is first BOC protected to produce (<aS)-<a [[(1,1-dimethylethoxy)carbonyl]amino]-3-hydroxytricyclo [3.3.1.1$^{3,7}$]decane-1-acetic acid (Formula V) by treating IV with BOC$_2$O in the presence of base such as sodium hydroxide and separated via ethyl acetate (EtOAc) extraction to separate out free acid V. Alternatively, in place of ethyl acetate, isopropyl acetate/heptane may be employed to crystallize out free acid V.

A solution of Formula V compound in an appropriate organic solvent such as tetrahydrofuran (THF) (cooled to a temperature within the range from about −10 to about 0° C.) is treated with methanesulfonyl chloride (Mesyl Cl), and Hunig base (diisopropylethylamine or DIPEA) to form the corresponding methanesulfonic acid salt of V.

A coupling reaction is then used to couple (<aS)-<a[[(1,1-dimethylethoxy)carbonyl]amino]-3-hydroxytricyclo [3.3.1.1$^{3,7}$]decane-1-acetic acid (Formula V) methanesulfonic acid activated ester to (1S,3S,5S)-2-azabicyclo [3.1.0]hexane-3-carboxamide (Formula VI) (prepared as described in U.S. application Ser. No. 10/716,012 filed Nov. 18, 2003) in the presence of 1-hydroxybenzotriazole (HOBT) or other known coupling agent to produce 3-(aminocarbonyl)-<aS)-<a-(3-hydroxytricyclo[3.3.1.1$^{3,7}$]dec-1-yl)-<b-oxo-(1S,3S,5S)-2-azabicyclo[3.1.0]hexane-2-ethanecarbamic acid, 1,1-dimethylethyl ester (Formula II).

Starting amino acid compound IV is prepared as described in U.S. application Ser. No. 10/716,012 filed Nov. 18, 2003.

SCHEME 3

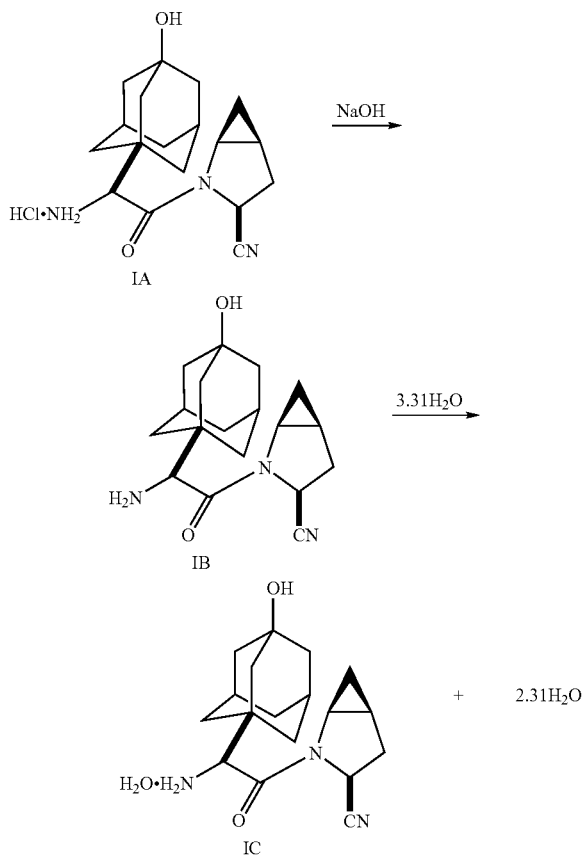

Referring to Scheme 3, the free base monohydrate IC may be formed from the BOC-protected intermediate IA as follows.

Hydrochloride salt IA is treated with sodium hydroxide or other base to form the free base IB. Free base IB may then be treated with water to form the free base monohydrate IC.

Dipeptidyl peptidase IV inhibition produced using the processes of the present invention are useful in the treatment of diabetes and complications thereof, hyperglycemia, Syndrome X, hyperinsulinemia, obesity, and atherosclerosis and related diseases as well as immunomodulatory diseases and chronic inflammatory bowel disease.

EXAMPLES

The following Examples represent preferred embodiments of the invention.

Example 1

3-Cyano-(<aS)-<a-(3-hydroxytricyclo[3.3.1.1$^{3,7}$]dec-1-yl)-<b-oxo-(1S,3S,5S)-2-azabicyclo[3.1.0]hexane-2-ethanecarbamic acid, 1,1-dimethylethyl ester (Formula II)

A. BOC Protection of (<aS)-<a-amino-3-hydroxytricyclo [3.3.1.1$^{3,7}$]decane-1-acetic acid (Formula IV) to form (<aS)-<a[[(1,1-dimethylethoxy)-carbonyl]amino]-3-hydroxytricyclo[3.3.1.1$^{3,7}$]decane-1-acetic acid, (V)

(<aS)-<a-amino-3-hydroxytricyclo[3.3.1.1$^{3,7}$]decane-1-acetic acid (Formula IV) (prepared as described in U.S. application Ser. No. 10/716,012, filed Nov. 18, 2003) (469 grams, 2.08 moles) was dissolved in ice cold 1 N NaOH (5 liters, 5 moles, 2.4 equivalents) in a phase splitter equipped with a temperature probe and a pH probe. THF (2.5 liters) was added to the solution. Solid Boc$_2$O was then added and the reaction mixture was stirred at ambient temperature for approximately 1 hour. EtOAc (4 liters) was then added with stirring and the resulting organic and aqueous layers were separated. The pH of the aqueous layer was adjusted to 7 with concentrated HCl. EtOAc (4 liters) was then added and additional HCl was added to lower the pH to approximately 1. The total volume of concentrated HCl added was 510 ml. The organic and aqueous layers were again separated and the aqueous layer was extracted with EtOAc (3×3 liters). The organic layers were then combined and washed with water (3 liters) and brine (3 liters). The washed organic layer was then dried with Na$_2$SO$_4$ and concentrated on a rotovap at room temperature until dryness. The yield was 542 grams of (<aS)-<a[[(1,1-dimethylethoxy)carbonyl]amino]-3-hydroxytricyclo[3.3.1.1$^{3,7}$]decane-1-acetic acid (Formula V).

B. 3-Cyano-(<aS)-<a-(3-hydroxytricyclo[3.3.1.1$^{3,7}$]dec-1-yl)-<b-oxo-(1S,3S,5S)-2-azabicyclo[3.1.0]hexane-2-ethanecarbamic acid, 1,1-dimethylethyl ester (Formula II)

A 2 L three-necked flask equipped with a thermometer, a mechanical stirrer and a gas inlet was charged with Part A (<aS)-<a[[(1,1-dimethylethoxy)carbonyl]amino]-3-hydroxytricyclo[3.3.1.1$^{3,7}$]decane-1-acetic acid (Formula V) (50 grams, 153.8 mmol). THF (200 ml) was added and stirred to produce a clear solution. The solution was cooled to −6° C. in an acetone-dry ice-water bath. Methanesulfonyl chloride (Mes-Cl) (13.1 ml, 169 mmol, 1.1 equivalents) was then added as a single portion followed by diisopropylethylamine (94 ml, 539 mmol, 1.1 equivalents). The diisopropylethylamine was added slowly over a period of about 4 minutes to keep the internal temperature below 8° C. The reaction mixture was stirred at 0° C. until all acid was converted to mixed anhydride. (1S,3S,5S)-2-azabicyclo[3.1.0]hexane-3-carboxamide hydrochloride salt (32.5 grams, 200 mmol, 1.1 equivalents) and hydroxybenzotriazole (HOBT) (1.04 grams, 7.6 mmol, 0.05 equivalents) were then added in a single portion and the flask was removed from the cooling bath. The reaction mixture was stirred at room temperature for 2 hours and then left overnight at room temperature. The reaction mixture was worked up by adding ethyl acetate and 1N aqueous HCl and brine. The organic layer was separated and washed with 20% aqueous KHCO$_3$ two times and then concentrated to a residue which was dried at 25° C. overnight. The retention time of the residue by HPLC was similar to an authentic sample of the amide II.

Example 2

Preparation of Free Base Compound IB by Direct Dehydration of Example 1 Amide in a Single Pot

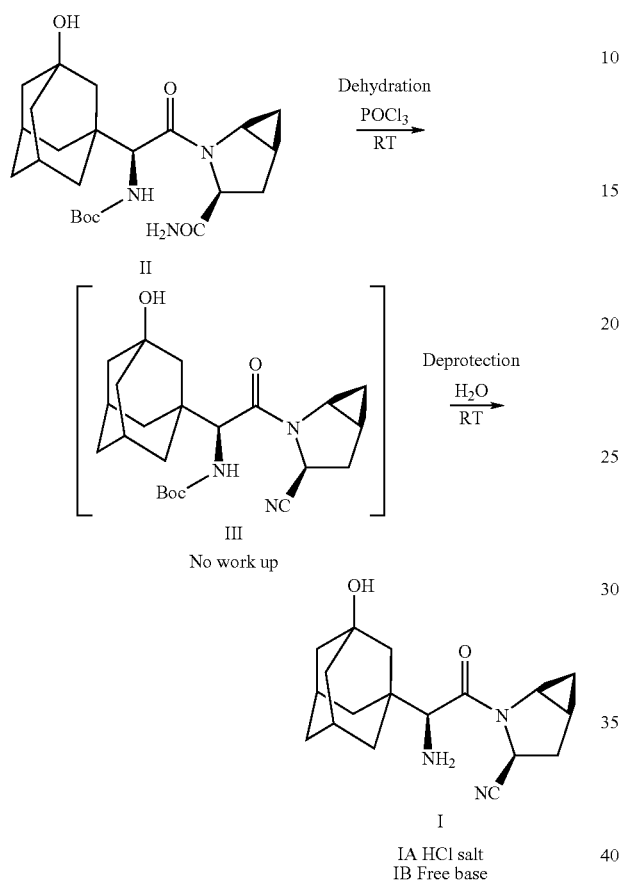

IA HCl salt
IB Free base

Example 1 amide compound II (433 mg) was dissolved in dichloromethane (2 mL) and phosphorus oxychloride (306 mg, 0.183 mL, 2 equiv) was added to it at room temperature. The reaction mixture was stirred at room temperature for 2.5 h. HPLC of the reaction mixture suggested 3% of Example 1 amide compound II present in it. The reaction mixture was diluted with additional dichloromethane (2 mL) followed by the addition of phosphorus oxychloride (150 mg, 0.09 mL, 1 equiv). The reaction mixture was stirred at room temperature for an additional 1 h. HPLC showed the absence of Example 1 compound II in the reaction mixture.

The reaction mixture was cooled to <5° C. and was slowly quenched by a dropwise addition of water (~10 mL), followed by stirring for 1 h at room temperature until compound III disappeared in the reaction mixture. The reaction mixture was cooled to <5° C. and carefully basified to pH 9 by the addition of 10 N NaOH. Sodium chloride (5 g) was added as solid and the organic layer was separated. The aqueous layer was re-extracted with dichloromethane (3×10 mL). The combined organic layers were concentrated under vacuum at 25° C. to leave a white foamy residue, which was dried at 25° C. under vacuum for 16 h to give free base compound IB, 220 mg, 95% pure, 70% yield from Example 1 compound II. MS: m/e 316 (M+1)$^+$, 338 (M+Na)$^+$, 356 (M+Na+H$_2$O)$^+$, 360 (M–H+2 Na)$^+$, 436 (M+Na+H$_3$PO$_4$)$^+$, 653 (2M+Na)$^+$, 671 (2 M+Na+H$_2$O)$^+$. The retention time of this product by HPLC was similar to authentic sample of free base compound IB. $^1$H NMR and $^{13}$CMR were in accordance with the structure for the free base IB.

What is claimed is:

1. The process for preparing a compound of the structure

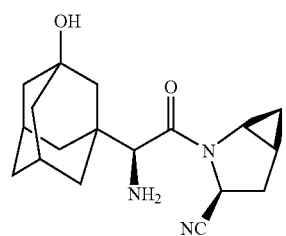

I which comprises
a) providing an amide of the structure II

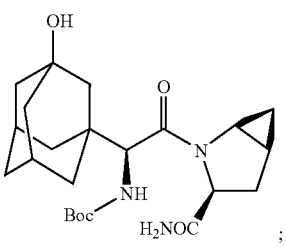

II b) reacting the amide II with phosphorus oxychloride in an organic solvent; and
c) treating the reaction mixture with water to form the product I in the form of its hydrochloride salt.

2. The process as defined in claim 1 wherein in step b) the amide II is reacted with phosphorus oxychloride in an organic solvent to form cyano compound III

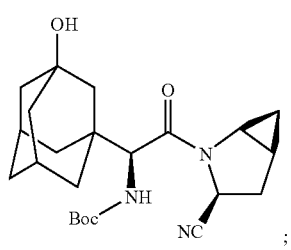

III and
in step c) without isolating cyano compound III, the cyano compound III is treated with water to form the product I in the form of its hydrochloric acid salt.

3. The process as defined in claim 2 further including the step of treating the hydrochloric acid salt of product I with base to form the corresponding free base.

4. The process as defined in claim 3 wherein the acid salt is treated with an alkali metal base to a pH of at least about 7.0.

5. The process as defined in claim 2 in the form of a one-pot process where the cyano compound III is not recovered.

6. The process as defined in claim 1 wherein the reaction of amide II and phosphorus oxychloride is carried out in the presence of dichloromethane as the organic solvent.

7. The process as defined in claim 1 wherein the reaction mixture is cooled to below about 5° C. and treated with water to form the hydrochloride salt.

8. The process as defined in claim 1 wherein the reaction of amide II with phosphorus oxychloride is carried out in one pot in dichloromethane.

9. The process as defined in claim 7 wherein the reaction of amide II with phosphorus oxychloride is carried out at room temperature to form an intermediate compound of the structure

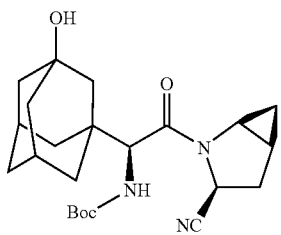

III which without isolating is treated with water to form the compound I in the form of its free base.

10. The process as defined in claim 3 wherein the reaction mixture containing the hydrochloride salt is cooled to below about 5° C. and treated with base to form the free base.

11. The process as defined in claim 10 wherein the base is an alkali metal hydroxide and the reaction mixture is basified to a pH from about 7.0 to about 14.0.

12. The process as defined in claim 1 wherein the phosphorus oxychloride is employed in a molar ratio to amide II within the range from about 1:1 to about 99:1.

13. The process as defined in claim 1 carried out in one pot employing about 3 equivalents of phosphorus oxychloride to about one equivalent of amide II.

14. The process as defined in claim 13 carried out in the presence of dichloromethane.

15. The process as defined in claim 14 wherein the reaction mixture is quenched with water to form the product I in the form of its hydrochloric acid salt.

16. The process as defined in claim 15 wherein the reaction mixture is basified with NaOH to about pH 9 and the product I is recovered in the form of its free base.

* * * * *